US012564337B2

(12) United States Patent
Huang et al.

(10) Patent No.: US 12,564,337 B2
(45) Date of Patent: Mar. 3, 2026

(54) RECURRENT NEURAL NETWORK FOR TUMOR MOVEMENT PREDICTION

(71) Applicant: Rensselaer Polytechnic Institute, Troy, NY (US)

(72) Inventors: Zhaoran Huang, Clifton Park, NY (US); Alex Hollingsworth, Syracuse, NY (US); Clare Thiem, Clinton, NY (US); Nathan McDonald, Ava, NY (US); Zhizhuo Liang, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 1108 days.

(21) Appl. No.: 17/188,312

(22) Filed: Mar. 1, 2021

(65) Prior Publication Data

US 2021/0267487 A1 Sep. 2, 2021

Related U.S. Application Data

(60) Provisional application No. 62/983,097, filed on Feb. 28, 2020.

(51) Int. Cl.
| | |
|---|---|
| *A61B 5/113* | (2006.01) |
| *A61B 5/00* | (2006.01) |
| *G06N 3/044* | (2023.01) |
| *G06N 3/08* | (2023.01) |
| *G16H 50/00* | (2018.01) |
| *G16H 50/20* | (2018.01) |

(52) U.S. Cl.
CPC ............ *A61B 5/113* (2013.01); *A61B 5/7267* (2013.01); *G06N 3/044* (2023.01); *G06N 3/08* (2013.01); *G16H 50/00* (2018.01); *G16H 50/20* (2018.01)

(58) Field of Classification Search
CPC ...... A61B 5/113; A61B 5/7267; G06N 3/044; G06N 3/08; G16H 50/20
USPC .......................................................... 706/12
See application file for complete search history.

(56) References Cited

U.S. PATENT DOCUMENTS

| | | | |
|---|---|---|---|
| 9,014,424 | B2 | 4/2015 | Berlinger et al. |
| 9,314,648 | B2 | 4/2016 | Li et al. |
| 9,669,236 | B2 | 6/2017 | Raleigh et al. |
| (Continued) | | | |

FOREIGN PATENT DOCUMENTS

| | | | |
|---|---|---|---|
| CN | 105931262 A | * | 9/2016 |
| EP | 3456383 A1 | | 3/2019 |
| WO | 2014203038 A1 | | 12/2014 |

*Primary Examiner* — Stephen S Hong
*Assistant Examiner* — Broderick C Anderson
(74) *Attorney, Agent, or Firm* — Barclay Damon LLP; Anthony P. Gangemi

(57) ABSTRACT

In an embodiment, there is provided a method of predicting respiratory motion in real-time. The method includes training, by a training module, a recurrent neural network circuitry in real time. The training is based, at least in part, on a training data set. The training data set includes a first number of motion samples. The motion samples are related to respiratory motion of a patient target region. The method further includes predicting, by the trained recurrent neural network circuitry, a future motion of the patient target region at a future point in time based, at least in part, on a prediction data set. The future point in time is a look ahead time period in the future relative to a prediction data window. The prediction data set includes a second number of motion samples.

20 Claims, 4 Drawing Sheets

(56)     References Cited

U.S. PATENT DOCUMENTS

| | | | |
|---|---|---|---|
| 9,911,199 B2 | 3/2018 | Vilsmeier | |
| 2006/0074292 A1* | 4/2006 | Thomson | A61B 6/12 |
| | | | 600/411 |
| 2010/0198101 A1* | 8/2010 | Song | A61B 5/0871 |
| | | | 600/547 |
| 2014/0012061 A1 | 1/2014 | Song et al. | |
| 2015/0134263 A1 | 5/2015 | Maeno et al. | |
| 2017/0216625 A1* | 8/2017 | Pishdad | A61N 5/1064 |
| 2018/0011459 A1* | 1/2018 | Boettcher | G05B 23/024 |
| 2018/0326223 A1 | 11/2018 | Willcut et al. | |
| 2019/0220986 A1 | 7/2019 | Magro et al. | |
| 2021/0097373 A1* | 4/2021 | Dunning | G06N 3/092 |
| 2021/0264242 A1* | 8/2021 | Canaday | G06N 3/063 |

* cited by examiner

RECURRENT NEURAL NETWORK FOR TUMOR MOVEMENT PREDICTION

CROSS REFERENCE TO RELATED APPLICATION(S)

This application claims the benefit of U.S. Provisional Application No. 62/983,097, filed Feb. 28, 2020, which is incorporated by reference as if disclosed herein in its entirety.

GOVERNMENT LICENSE RIGHTS

This invention was made with government support under grant number FA8750-15-3-6000, awarded by the Air Force Research Laboratory, and under contract number SA2018-UP-020-NOA, with the Air Force Research Laboratory. The government has certain rights in the invention.

FIELD

The present disclosure relates to tumor movement prediction, in particular to, a recurrent neural network for tumor movement prediction.

BACKGROUND

Respiratory motion is a well-recognized challenge in chest and upper abdominal imaging (e.g., computerized tomography (CT) scan, magnetic resonance imaging (MRI), mammography), and radiation therapy for tumors included in chest or upper abdominal organs (e.g., lung, liver, throat, stomach, breast and/or pancreas). Tumor motion caused by respiration may follow a relatively complex moving trajectory driven by a patient breathing pattern. Patient respiration may vary over time in one session or between sessions for the same patient and may differ significantly between patients. For example, the patient may cough or sneeze, and/or a respiration pattern may change as the patient experiences pain. In some situations, artificial intelligence-based machine learning algorithms may be utilized to predict respiratory motion. The variation in patient respiration may include variation in amplitude and/or frequency and may result in drift in a location of a targeted tumor during a treatment session. Such drift may then result in exposure of healthy tissue to radiation and/or reduced efficiency for the targeted tumor. Conventional techniques for counteracting respiratory motion may include breath-hold, passive motion tracking and respiration gating (wait) methods. The conventional techniques may result in patient discomfort and/or increased treatment time and thus increased radiation exposure.

SUMMARY

In an embodiment, there is provided a method of predicting respiratory motion in real-time. The method includes training, by a training module, a recurrent neural network circuitry in real time. The training is based, at least in part, on a training data set. The training data set includes a first number of motion samples. The motion samples are related to respiratory motion of a patient target region. The method further includes predicting, by the trained recurrent neural network circuitry, a future motion of the patient target region at a future point in time based, at least in part, on a prediction data set. The future point in time is a look ahead time period in the future relative to a prediction data window. The prediction data set includes a second number of motion samples.

In some embodiments, the method further includes updating, by the training module, the training of the recurrent neural network circuitry, at an update time interval. The updating is based, at least in part, on a current internal state of the recurrent neural network circuitry.

In some embodiments of the method, the updating includes determining a plurality of output weight values using a sliding training data window corresponding to the first number of motion samples.

In some embodiments of the method, the prediction data window corresponds to a sliding window.

In some embodiments of the method, a length of the look ahead time period is related to a latency of imaging and/or therapeutic equipment. In some embodiments of the method, the update time interval is related to a motion data sample interval.

In some embodiments of the method, the recurrent neural network corresponds to a reservoir computing network.

In some embodiments of the method, a time duration of the training data window is less than or equal to 30 seconds. In some embodiments of the method, the second number of motion samples is in the range of 5 to 20. In some embodiments of the method, the motion data sample rate is in the range of 10 to 40 samples per second.

In an embodiment, there is provided a system for predicting respiratory motion in real time. The system includes a system controller circuitry, a training module, and a recurrent neural network circuitry. The training module is configured to train the recurrent neural network circuitry in real time. The training is based, at least in part, on a training data set. The training data set includes a first number of motion samples. The motion samples are related to respiratory motion of a patient target region. The trained recurrent neural network circuitry is configured to predict a future motion of the patient target region at a future point in time based, at least in part, on a prediction data set. The future point in time is a look ahead time period in the future relative to a prediction data window. The prediction data set includes a second number of motion samples.

In some embodiments of the system, the training module is configured to update the training of the recurrent neural network circuitry, at an update time interval. The updating is based, at least in part, on a current internal state of the recurrent neural network circuitry.

In some embodiments of the system, the updating includes determining a plurality of output weight values using a sliding training data window corresponding to the first number of motion samples.

In some embodiments of the system, the prediction data window corresponds to a sliding window.

In some embodiments of the system, a length of the look ahead time period is related to a latency of imaging and/or therapeutic equipment. In some embodiments of the system, the update time interval is related to a motion data sample interval.

In some embodiments of the system, the recurrent neural network corresponds to a reservoir computing network.

In some embodiments of the system, a time duration of the training data window is less than or equal to 30 seconds.

In some embodiments of the system, the prediction second number of motion samples is in the range of 5 to 20.

In some embodiments of the system, the motion data sample rate is in the range of 10 to 40 samples per second.

BRIEF DESCRIPTION OF DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

Figure 1:
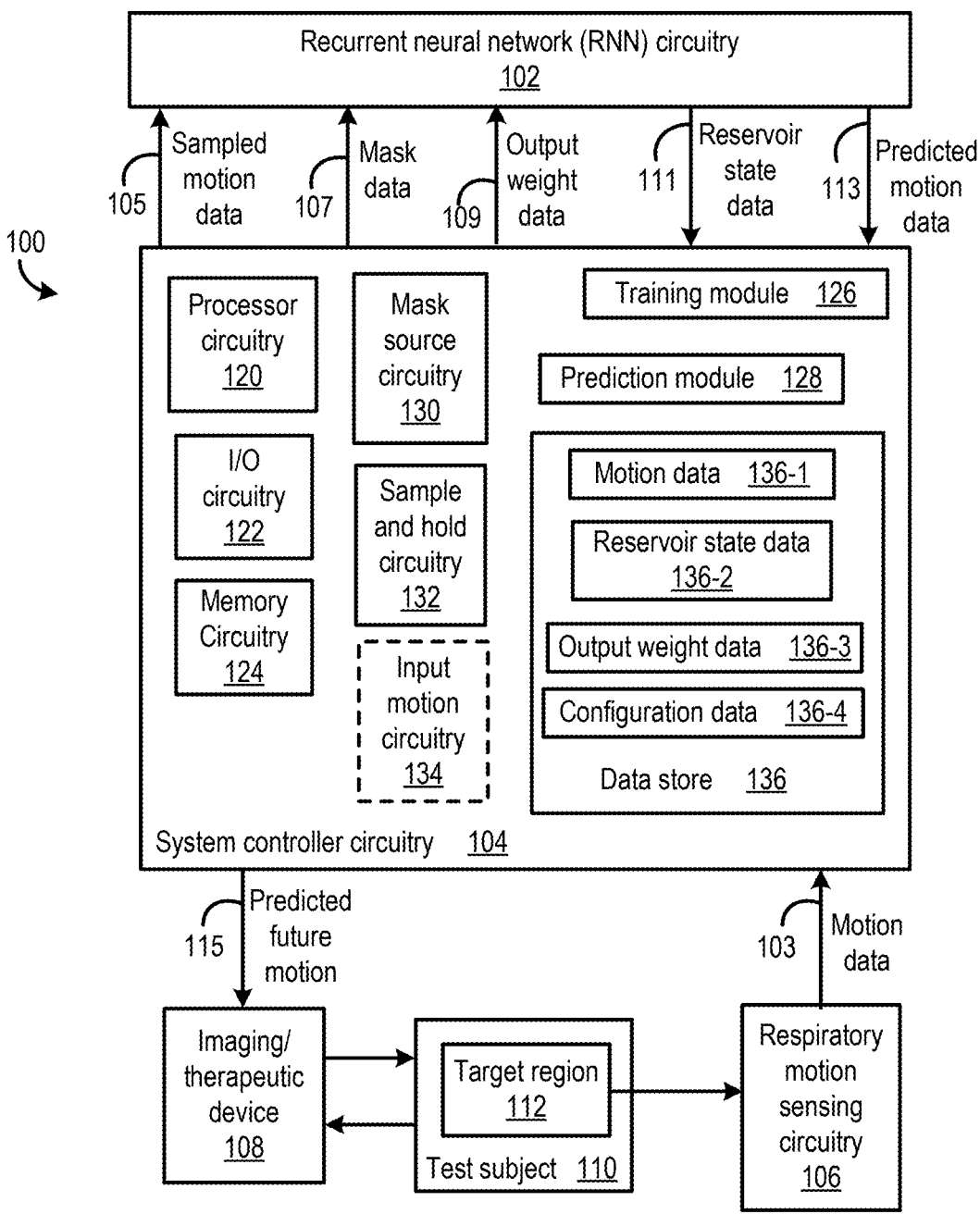
FIG. 1 illustrates a functional block diagram of a system for tumor movement prediction, consistent with several embodiments of the present disclosure.

Although the following Detailed Description will proceed with reference being made to illustrative embodiments, many alternatives, modifications, and variations thereof will be apparent to those skilled in the art.

DETAILED DESCRIPTION

A recurrent neural network (RNN) is a class of artificial neural network where present network outputs may be influenced by past events. RNNs may thus be configured to model dynamics of sequential signals, time varying signals, and/or temporal data, e.g., time varying data. An RNN may include, but is not limited to, a reservoir computing (RC) network. An RC network may include an input layer, a hidden layer, and output layer. Each layer may include one or more neurons or nodes. The RC hidden layer may correspond to a "reservoir" of neurons in fixed connections that may be random. The neurons in the reservoir may be recurrently, sparsely, statically, and/or randomly connected. In one nonlimiting example, the reservoir may be constructed from a time delay dynamic system. In another example, the reservoir may be constructed from a spatial-temporally changing dynamic system. A time delay reservoir may correspond to a delay line topology with a number (e.g., on the orders of 10, 100, or 1000) of neurons stored in a temporal domain as virtual nodes along the delay line. In another example, the reservoir may correspond to a true-time delay reservoir. Advantageously, during RC network training, only weights connecting the hidden layer to output layer neurons are updated. This simplicity in network topology supports relatively rapid execution suitable for real-time respiratory motion prediction. An associated relatively compact physical implementation (e.g., on CMOS (complementary metal oxide semiconductor) or silicon photonics or other integrated platform) of the RC network may provide speed, size, weight, and power (SWaP) efficiencies.

An RC network may be implemented in circuitry (that may be programmable), firmware and/or software and, in some situations, at least a portion of the RC network may be implemented in the optical domain. In some embodiments, the RC network may include a photonic true-time delay reservoir (TDR). As used herein, "true time delay" means that a time delay of the reservoir includes intrinsic time delays of the electronic components and the optical components included in the reservoir and a time delay introduced into the reservoir by a fiber spool. A true-time delay may correspond to a characteristic of the system and may correspond to a minimum time delay. The RC network, including the true time delay reservoir may be configured for, for example, real-time respiratory motion prediction.

Generally, during training, an RC network is configured to learn a desired expected value of an l-dimensional output y(k) as a function of an n-dimensional input u(k), given data sequence(s) of length k=1, 2 . . . , K. The n-dimensional input u(k) may then correspond to a sampled version of a continuous input signal u(t), with a sample period, t, e.g., using a sample and hold technique configured to digitize a continuous signal into discrete data. The reservoir may correspond to an N-dimensional space x(k) and the input u(k) may be projected into the reservoir. N may be greater than K. For a selected discrete time input u(k), the reservoir state may then be expressed in an evolution equation form as:

$$x(k)=f(\beta W_{in}u(k)+\alpha W_{res}x(k-1)+\psi) \qquad (1)$$

where $f$ is a nonlinear transfer function of the reservoir, $\beta$ is input gain, a is attenuation of the reservoir state, $\varphi$ corresponds to a bias vector, $W_{in}$ is an n×N matrix of random projection weights between the input layer neurons and the reservoir, and $W_{res}$ is an N×N matrix describing the internal connections and individual weights of the reservoir neurons. Both $\alpha$ and $\beta$ may be on the interval [0,1]. The form of the evolution equation may be related to a physical layer implementation.

The RC response ŷ(k) (e.g., predicted future motion) may then be a linear sum of the weighted reservoir output neurons:

$$\hat{y}(k)=W_{out}S(k), \qquad (2)$$

where S(k) is an (N+1)×K matrix concatenating the reservoir states x(k) with a fixed output bias neuron of value 1 and $W_{out}$ is an l×(N+1) matrix of trained output weights. Using the target output y(k) for the training examples, $W_{out}$ may be calculated directly by minimizing a Mean Squared Error (MSE) between the target output y(k) and the reservoir output via, for example, a regression as:

$$W_{out}=yS^T(SS^T+\lambda I)^{-1} \qquad (3)$$

where T denotes transpose, $\lambda$ is a regularization factor, and/is an identity matrix. It may be appreciated that the most computationally expensive operation is the initial matrix inverse calculation.

Generally, this disclosure relates to a system for tumor movement prediction. A tumor may be included in or may correspond to a target region in a patient. A motion and corresponding position of the target region may vary over the imaging/therapeutic session due, in part, to patient respiration. Thus, predicting tumor movement may correspond to predicting respiratory motion. In an embodiment, a system may be configured to capture respiratory motion data and to predict, in real time, a future motion of the target region. The future motion information may then be used to facilitate imaging and/or provision of therapeutic energy to the target region. In one nonlimiting example, the target region may correspond to a tumor that is to be irradiated. As is known, adult respiration, at rest, may typically be the range of 10 to 20 breaths per minute. The respiration of infants and young children is generally higher. Adult respiration may similarly be higher in some situations. Thus, although generally periodic, respiration may vary. For example, respiration of a patient under treatment may be in the range of 3 to 25 breaths per minute.

In an embodiment, the predicting may be performed by a recurrent neural network (RNN) circuitry that has been trained, in real time, using patient respiratory motion data. The training may be updated using a sliding window of motion data, to reflect relatively more current patient respiration and corresponding target region motion data. As used herein, "real time" means training of the recurrent neural network circuitry may be performed in less than a duration of one sampling time interval, i.e., one motion data sample interval. Subsequent updating may be performed during each sampling time interval. A size of the sampling time interval may be related to characteristics of a motion monitoring system. In one nonlimiting example, the sampling time interval may be on the order of tens of milliseconds. However, this disclosure is not limited in this regard.

Thus, patient respiration may be accommodated and the imaging/therapeutic devices may continue to accurately target the patient target region in the presence of patient respiration. Training and updating in real time are configured to capture relatively current respiration data and to facilitate relatively accurately predicting target region motion. Thus, imaging or irradiating non-target regions may be reduced or avoided.

In an embodiment, there is provided a method of predicting respiratory motion in real-time. The method includes training, by a training module, a recurrent neural network circuitry in real time. The training is based, at least in part, on a training data set. The training data set includes a first number of motion samples. The motion samples are related to respiratory motion of a patient target region. The method further includes predicting, by the trained recurrent neural network circuitry, a future motion of the patient target region at a future point in time based, at least in part, on a prediction data set. The future point in time is a look ahead time period in the future relative to a prediction data window. The prediction data set includes a second number of motion samples.

FIG. 1 illustrates a functional block diagram of a system 100 for tumor movement prediction, consistent with several embodiments of the present disclosure. System 100 includes a recurrent neural network (RNN) circuitry 102 and a system controller circuitry 104. System 100 may include or may be coupled to a respiratory motion sensing circuitry 106. Respiratory motion sensing circuitry 106 is configured to detect motion of target region 112 that may be due to or related to respiration of a test subject 110. System 100 may be coupled to an imaging/therapeutic device 108. Imaging/therapeutic device 108 is configured to image and/or provide therapeutic radiation to the test subject 110 and, in particular, to a target region 112. Imaging/therapeutic device 108 may include, but is not limited to an x-ray scanner, a computed tomography (CT) scanner, a magnetic resonance imaging (MRI) scanner, a proton scanner, etc.

Test subject 110 may correspond to a patient and target region 112 may correspond to at least a portion of the patient that is to be imaged and/or is to receive therapeutic radiation. In one nonlimiting example, target region 112 may correspond to a tumor that is to be imaged and/or irradiated. It may be appreciated that patient respiration may cause the target region 112 to move during imaging and/or provision of therapeutic radiation. Such respiratory motion may result in imaging only a portion of the target region 112 and/or unintentionally irradiating tissue adjacent the target region 112.

Respiratory motion sensing circuitry 106 may be positioned in or on test subject 110 relative to target region 112. Respiratory motion sensing circuitry 106 may be configured to capture the respiratory motion continuously and/or discretely, over time, and to provide corresponding motion data 103 to system controller circuitry 104. The motion data 103 corresponds to u(t), as described herein. A motion sample may then be u(k) that corresponds to a sampled u(t), sampled with a sample period, t, as described herein. The motion data 103 may thus represent respiratory motion and corresponding motion of the target region 112 caused by the respiratory motion.

In one embodiment, recurrent neural network (RNN) circuitry 102 may correspond to, for example, an RC network. Generally, RNN 102 is configured to receive sampled motion data 105 (i.e., motion samples) corresponding to motion data 103 from system controller circuitry 104 and to provide a predicted motion data 113 as output, as will be described in more detail below.

System controller circuitry 104 includes processor circuitry 120, input/output (I/O) circuitry 122, and memory circuitry 124. System controller circuitry 104 may further include a training module 126 and a prediction module 128. System controller circuitry 104 may further include mask source circuitry 130, sample and hold circuitry 132, and a data store 136. In some embodiments, system controller circuitry 104 may include input motion circuitry 134. In some embodiments, respiratory motion sensing circuitry 106 and/or input motion circuitry 134 may include a Gaussian filter configured to reduce noise that may be present in the data 103.

The data store 136 may be included, for example, in memory circuitry 124, and may be configured to store one or more of motion data 136-1, reservoir state data 136-2, output weight data 136-3, and/or configuration data 136-4. Motion data 136-1 may include one or more sets of motion data 103 received from motion sensing circuitry 106. Reservoir state data 136-2 may include reservoir state data 111 captured from recurrent neural network circuitry 102, as will be described in more detail below. Output weight data 136-3 may include one or more sets of output weight data (e.g., output weight matrix, $W_{out}$) determined based, at least in part, on motion data, as will be described in more detail below. Configuration data 136-4 may include, for example, type and characteristic data associated with imaging/therapeutic device 108. Such characteristic data may then be utilized to determine an appropriate future time for a prediction of target region motion.

System controller circuitry 104 may generally be implemented in circuitry, and may further include software and/or firmware. In an embodiment, system controller circuitry 104 may be implemented in programmable circuitry including, for example, a field-programmable gate array (FPGA). For example, the system controller circuitry 104 may be implemented in an off-line computing resource.

In operation, system controller circuitry 104 may be coupled to recurrent neural network circuitry 102 and may be configured to manage operation of RNN 102. System controller circuitry 104 may be configured to provide data to and receive data from recurrent neural network circuitry 102. System controller circuitry 104 may be configured to receive motion data 103 from respiratory motion sensing circuitry 106. The motion data 103 may then be stored in data store 136 as motion data 136-1. System controller circuitry 104 may then be configured to provide sampled motion data 105 and mask data 107 to recurrent neural network circuitry 102, as will be described in more detail below. System controller circuitry 104 may be configured to receive predicted motion data 113 from recurrent neural network circuitry 102 and to provide a predicted future motion 115 to imaging/therapeutic device 108. System controller circuitry 104 may be further configured to provide output weight data 109 to, and to capture reservoir state data 111 from, recurrent neural network circuitry 102.

Training module 126 is configured to manage training recurrent neural network circuitry 102, as will be described in more detail below. Prediction module 128 may be configured to provide a predicted future motion 115 of target region 112 to imaging/therapeutic device 108. The predicted future motion 115 may correspond to predicted motion data 113 received from recurrent neural network circuitry 102, as will be described in more detail below.

Training module 126 may be further configured to manage updating the training of the recurrent neural network circuitry 102, in real time, at an update time interval. The updating may be based, at least in part, on a current internal state of the recurrent neural network, i.e., reservoir state data 111. In an embodiment, the update time interval may correspond to a sample time interval associated with motion samples.

Computationally, operations of system 100 may be described as follows. Continuous motion data 103 may correspond to an input signal u(t). Thus, a continuous time input signal u(t) may be sampled at a sample rate yielding a corresponding discrete sequence, u(k), that includes a sequence of motion samples. The sample rate may correspond to motion data sample rate, as described herein. A sample time interval i.e., 1/(sample rate), may thus have time duration, $\tau$. Sample and hold circuitry 132 may be configured to sample and hold the input signal with a sample and hold period of length, $\tau$. Mask source circuitry 130 may then be configured to generate a mask function m(t) that may be based, at least in part, on a random distribution. The mask function may then be sampled to provide $W_{in}$, a matrix of random projection weights, as described herein. In one embodiment, $W_{in}$ may be provided to RNN 102 as mask data 107. In another embodiment, input motion circuitry 134 may be configured to combine the mask data with the sampled motion data 105 and to provide the result to RNN 102. The sampled motion data 105 and mask data 107 may then be coupled to the RNN via a nonlinear node, as described herein.

It may be appreciated that the RNN 102 may include a reservoir and the reservoir is a dynamic system that can be described by a delayed differential equation, e.g., Eq. (1), that includes a nonlinear function, $f$. In one nonlimiting example, $f$ may correspond to a $\sin^2$ function. The evolution equation of the reservoir states x(k) of the RNN 102 may correspond to Eq. (1). The reservoir state data 111 may thus correspond to reservoir states x(k).

Training module 126 may be configured to determine the output weight matrix $W_{out}$ (i.e., output weight data 109) based, at least in part, on reservoir state data 111 that corresponds to x(k). It may be appreciated that determining the output weight matrix corresponds to training RNN 102. Initially, training may be performed over a training data window and may be based, at least in part, on a training data set. A training data window size corresponds to a training data set length. The training data set may include a first number of motion samples. In one nonlimiting example, the first number of motion samples may be on the order of 100, e.g., 500. However, this disclosure is not limited in this regard. A time duration of the training data window and a corresponding size of the training data set may be related to a prediction accuracy. In one nonlimiting example, the duration of the training data window may be less than 30 seconds. However, this disclosure is not limited in this regard. The first number of motion samples may be related to the duration of the training data window by a motion data sample rate. In some embodiments, the motion data sample rate may be related to the sample and hold period associated with the RNN.

The output weight matrix may be determined via, for example, a regression. The regression, may include, but is not limited to, a ridge regression or a linear regression. Thus, $W_{out}$ may be determined by minimizing a mean squared error (MSE) between a target output y(t) and a predicted $\hat{y}(1)$, (Eq. (3)). As used herein, a target (i.e., measured) output y(t) corresponds to a future motion of the patient target region at a future point in time that is a look ahead time period in the future relative to a prediction data window. The target output may be included in a training data set that may be stored in motion data 136-1, for example. The output weight matrix $W_{out}$ (i.e., output weight data 109) may then be provided to RNN 102. The predicted motion data 113 may then correspond to an output of RNN 102, i.e., $\hat{y}(k)$, a linear sum of the weighted reservoir output neurons (Eq. (2)), weighted by the output weight data 109.

Thus, system 100 (i.e., RNN 102 and system controller circuitry 104) may be configured to receive motion data corresponding to motion of target region 112 related to respiration. The motion data may be sampled and held to yield sampled motion data and a mask function may be configured to provide mask data. The sampled motion data 105 and the mask data 107 may then be provided to RNN 102. Training includes determining the output weight matrix based, at least in part, on the input motion data, u(t), and based, at least in part on target motion data. The target motion data, y(t), corresponds to a time in the future relative to the input motion data, u(t).

After training, i.e., after determining the output weight data 109 ($W_{out}$), prediction module 128 may be configured to utilize RNN 102 to predict a future motion of the patient target region at a future point in time. The prediction may be based, at least in part, on a prediction data set. The prediction data set corresponds to a prediction data window that may correspond to a sliding window. The prediction data set may include a second number of motion samples that may be captured and stored in motion data 136-1. In one nonlimiting example, the second number of motion samples may be on the order of 10, e.g., may be 15. However, this disclosure is not limited in this regard. The future point in time may correspond to a look ahead time period in the future relative to a prediction data window, as described herein. Thus, the trained RNN 102 may be configured to predict the future motion of the patient target region at the future point in time based, at least in part, on the prediction data set.

In an embodiment, the output data matrix, $W_{out}$, may be updated as motion data is acquired during an imaging/treatment session. In other words, after initial training that determines an initial output data matrix, $W_{out}$, as new motion data is captured, $W_{out}$ may be updated and the updated output data matrix may then be used by the RNN to predict the future motion.

Figure 2:
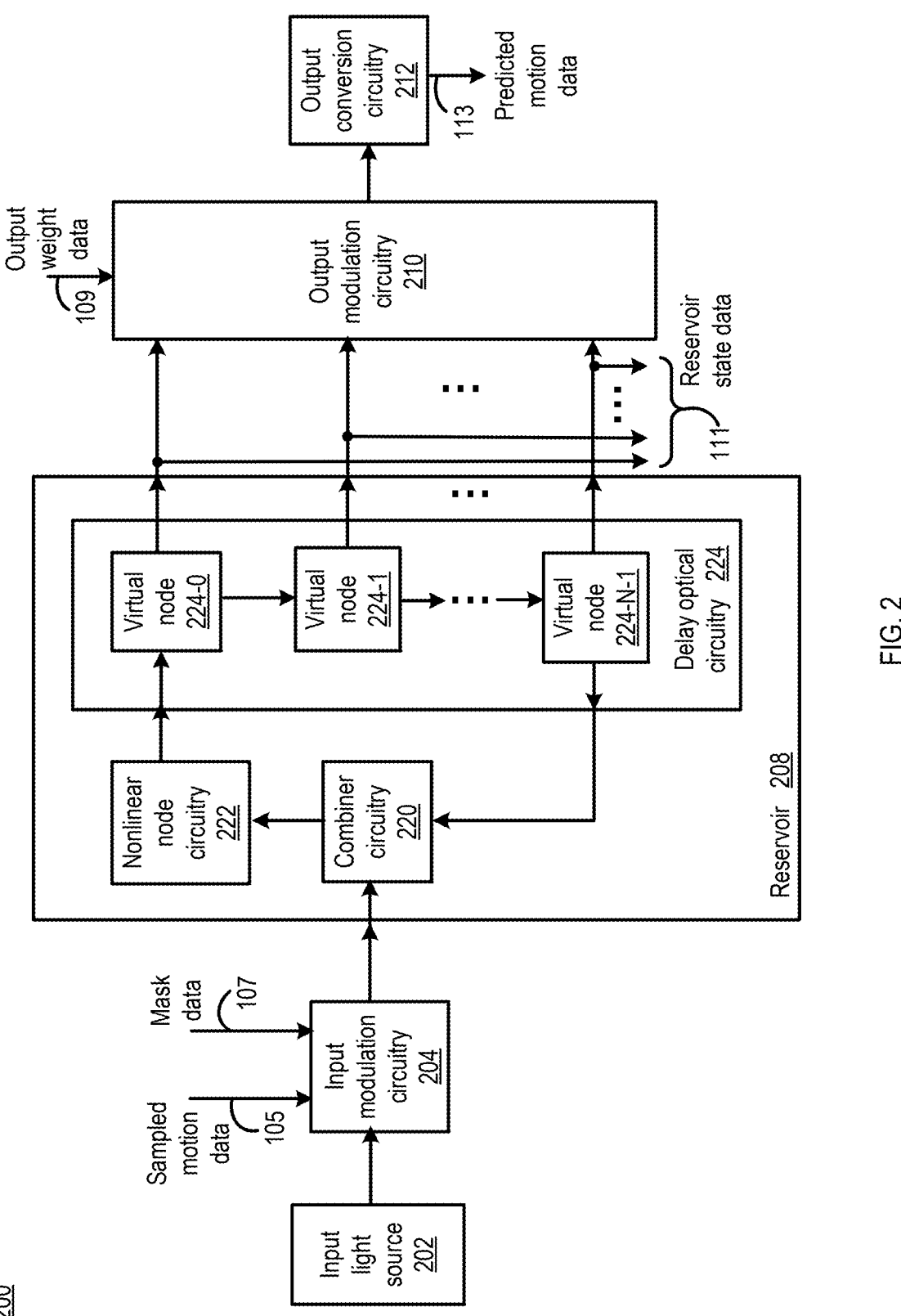
FIG. 2 illustrates a functional block diagram of an example recurrent neural network consistent with several embodiments of the present disclosure.

FIG. 2 illustrates a functional block diagram of an example recurrent neural network (RNN) 200 consistent with several embodiments of the present disclosure. RNN 200 is one example of recurrent neural network circuitry 102 of FIG. 1. RNN 200 includes an input light source 202, input modulation circuitry 204, a reservoir 208, output modulation circuitry 210, and output conversion circuitry 212. For example, reservoir 208 may correspond to an optical reservoir and RNN 200 may then correspond to an optical reservoir computing device. Reservoir 208 includes a combiner circuitry 220, nonlinear node circuitry 222, and delay optical circuitry 224. Delay optical circuitry 224 includes a plurality of virtual nodes 224-0, 224-1, . . . , 224-N−1. Input light source 202 and input modulation circuitry 204 may correspond to an input layer. Reservoir 208 may correspond to a reservoir layer. Output modulation circuitry 210 and output conversion circuitry 212 may correspond to an output layer of RNN 200.

A reservoir, e.g., reservoir 208, may include one or more nonlinear neurons. In an embodiment, reservoir 208 may correspond to a time delay reservoir (TDR) that may be configured as a ring topology that includes one nonlinear neuron (e.g., nonlinear node circuitry 222) and an arbitrary number N "virtual nodes", e.g., virtual nodes 224-0, 224-1, . . . , 224-N−1. The ring may then correspond to a delay line, e.g., including combiner circuitry 220, nonlinear node circuitry 222, and delay optical circuitry 224. The TDR may be configured to distribute information in time across the plurality of virtual nodes 224-0, 224-1, . . . , 224-N−1 in the delay line 224.

In an embodiment, reservoir 208 may correspond to a true-time delay reservoir, as described herein.

In an embodiment, the input signal to the reservoir 208 may be sampled and held for time τ. Time duration t may correspond to a duration of one round-trip through the delay line reservoir, e.g., reservoir 208. Then, for each sampled input u(k), the delay line with characteristic duration t may itself be sampled N+1 times with sample period θ, where τ=(N+1)θ. Each measurement, i.e., each delay line sample, may correspond to a virtual node, e.g., virtual nodes 224-0, 224-1, . . . , 224-N−1. As used herein, a virtual node may not have a defined physical location and may not be configured to perform computation on the signal. It may be appreciated that, while the reservoir may be configured such that N+1 virtual nodes are supported, typically only N of those virtual nodes are used for determining the reservoir state, x(k).

It may be appreciated that merely sampling u(k) over t would result in all virtual nodes, e.g., virtual nodes 224-0, 224-1, . . . , 224-N−1, having a same value. Thus, mask source circuitry 130 may be configured to provide a masking function of fixed arbitrary weights ($W_{in}$) that may then be applied to each u(k), as described herein. The result may be linearized and then sequentially fed to the reservoir, i.e., to combiner circuitry 220. In one nonlimiting example, the masking function may correspond to a uniform random mask with range [−1, +1]. However, this disclosure is not limited in this regard.

Input modulation circuitry 204 may be configured to receive light energy from input light source 202 and to modulate the received light based, at least in part, on sampled motion data 105 and mask data 107. In some embodiments, input light source 202 may correspond to a laser. In some embodiments, input light source 202 may correspond to a light-emitting diode. In one nonlimiting example, input modulation circuitry 204 may correspond to a Mach Zehnder modulator. However, this disclosure is not limited in this regard.

The modulated output of input modulation circuitry 204 may then be provided to reservoir 208 and the combiner circuitry 220. Combiner circuitry 220 may be further configured to receive an output of delay optical circuitry 224 and virtual node 224-N−1. An output of combiner circuitry 220 may then be provided to nonlinear node circuitry 222. In one nonlimiting example, nonlinear node circuitry 222 may be configured to implement a sin function. However, this disclosure is not limited in this regard. An output of nonlinear node circuitry 222 may then be provided to delay optical circuitry 224 and virtual node 224-0. An output of virtual node 224-0 may then be provided to virtual node 224-1 and so on to virtual node 224-N−1. A state of each virtual node may correspond to reservoir state data 111 that may be captured and provided to system controller circuitry 104, as described herein. The reservoir state data 111 may also be provided to output modulation circuitry 210. Output modulation circuitry 210 may be further configured to receive output weight data 109. For example, output weight data 109 may be received from system controller circuitry 104. Output modulation circuitry 210 may then be configured to modulate the reservoir state data 111 with the output weight data 109. It may be appreciated that output weight data 109 corresponds to an output weight matrix. An output of output modulation circuitry 210 may then be provided to output conversion circuitry 212. Output conversion circuitry 212 is configured to convert the output of output modulation circuitry 210 into predicted motion data 113. In one nonlimiting example, output conversion circuitry 212 may be configured to convert optical data into electrical data.

Thus, RNN 200 may be configured to receive sampled motion data 105 and mask data 107 and to provide, as output, predicted motion data 113.

It may be appreciated that prediction using neural networks generally includes training the neural network and then predicting using the trained neural network. Generally, training a neural network is relatively more computationally expensive compared to prediction operations using the neural network. A motion data set may generally include a sequence of samples of motion, corresponding to respiratory motion. An amount of samples is related to both the sample rate and a total time duration of the data set. For example, one minute of motion data captured at a sample rate of 33 samples per second yields 33 samples/sec×60 sec/minute×1 minute=1980 samples, or approximately 2000 samples. To facilitate training in a health care setting, an initial portion (e.g., initial training data set) of the motion data set may be used for training to determine an optimized but fixed $W_{out}$. The determined $W_{out}$ may then be used for motion prediction operations based, at least in part, on a remaining portion of the motion data. In one nonlimiting example, a motion data set of duration 2 minutes may be divided into an initial portion of duration 90 seconds (~3000 data points at 33 samples/sec) for training and the remaining 30 seconds for prediction operations.

It may be appreciated that a relatively longer training period with associated greater number of motion samples may result in a relatively better prediction accuracy. For example, the longer duration training data may include more breathing pattern variations so that the RNN may have more "memories" of any irregularities. Clinically, a longer data training session may result in an extended radiation treatment time and thus reduced efficiency. Additionally or alternatively, an extended training data set may result in over-fitting of the RNN model for some patients' breathing patterns. Additionally or alternatively, a patient's breathing pattern may change over time so that an earlier trained RNN may become less relevant as a prediction time becomes relatively more temporally distant from the training time.

Figure 3:
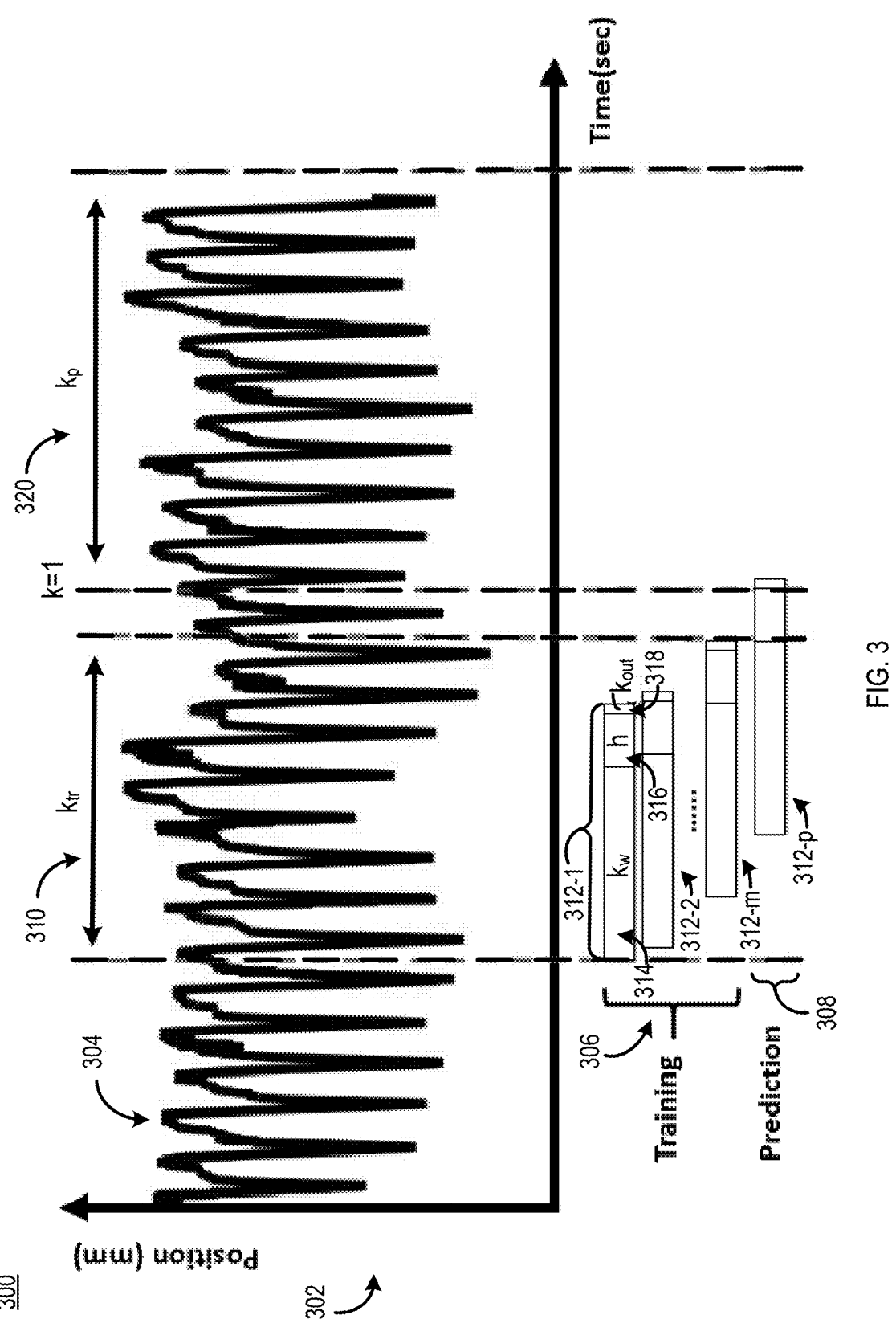
FIG. 3 is a timing diagram illustrating training and prediction, according to some embodiments of the present disclosure.

FIG. 3 is a timing diagram 300 illustrating training and prediction, according to some embodiments of the present disclosure. Timing diagram 300 includes a plot 302 with a horizontal axis corresponding to time in seconds and a vertical axis corresponding to position in millimeters. Timing diagram 300 further includes a motion waveform 304 corresponding to patient respiration. Timing diagram 300 includes a training data window 310 and a prediction region $k_p$ 320. Timing diagram 300 further includes a plurality of data blocks 312-1, 312-2, . . . , 312-$m$ and 312-$p$ configured to illustrate time periods related to training and prediction, as will be described in more detail below. The data blocks are grouped into a training group 306 and a prediction 308. Training group 306 may thus include data blocks 312-1, 312-2, . . . , 312-$m$ and prediction 308 includes data block 312-$p$. Each data block 312-1, 312-2, . . . , 312-$m$ and 312-$p$ includes a window of length $k_w$, that corresponds to a prediction data window 314; a look ahead time period 316 with length, h; and a prediction point (i.e., $k_{out}$) 318. The window length, $k_w$, may thus correspond to a second number of motion samples. Thus, a length of each data block may correspond to a number of motion samples (i.e., data points). The prediction data window 314 corresponds to a number of motion samples to be used for a prediction. The look ahead time period 316 corresponds to a number of sample periods between the prediction data window 314 (i.e., an end of the prediction data window 314) and the prediction 318.

In operation, the output weight matrix $W_{out}$ may be determined over the training data window 310. A length, $k_{tr}$, of the training data window 310 corresponds to a number of motion data points (i.e., samples) used for training the RNN. The motion data points used for training (i.e., $k_{tr}$ data points) may then correspond to a training data set. It may be appreciated that the number of data points used for training affects prediction performance. The length, $k_{tr}$, of the training data window 310 and, thus, the number of data points used for training are related to a time duration of the training data window by the motion data sample rate. In other words, the time duration of the training data window is equal to $k_{tr}$ divided by the motion data sample rate. In an embodiment, the number of data points, $k_{tr}$, may be in the range of 300 to 1000. In one embodiment, $k_{tr}$ may be 500. At a motion data sample rate of 33 samples/sec, $k_{tr}$=1000 corresponds to time duration of the training data window of about 30 seconds. In one nonlimiting example, $k_{tr}$ may be 500 data points (corresponding to a time duration of the training data window of about 15 seconds at motion data sample rate of 33 samples/sec). However, this disclosure is not limited in this regard. In other words, the motion data sample rate may be greater than or less than 33 samples/sec.

The length of the training data window $k_{tr}$ may be fixed at a selected value (e.g., 500) and may then correspond to a sliding window. In other words, the training may proceed based, at least in part, on the training data window and the training data window may be measured from a current time back in time for a window duration defined by $k_{tr}$. The training data window may be configured to slide through some or all of an imaging/therapeutic session. Thus, the training data set may correspond to a sliding window. In other words, with each new motion sample added to the training data set, an oldest motion sample may be dropped from the training data set. The training data set may be updated at the motion data sampling rate, e.g., 33 samples/ sec.

The output weight matrix $W_{out}$ may then be updated at approximately a sampling time interval corresponding to the motion data sampling rate, e.g., each 30 milliseconds for a sample rate of 33 samples/second. The output weight matrix may thus be configured to reflect a most recent breathing pattern and may be updated throughout the imaging/therapeutic session. It may be appreciated that a relatively smaller $k_{tr}$ may correspond to a relatively better computational efficiency, i.e., a relatively shorter time to determine, e.g., $W_{out}$.

Each data block 312-1, 312-2, . . . , 312-$m$ and 312-$p$ includes a prediction data window (i.e., window length, $k_w$) 314, a look ahead time period 316 with length, h, and a prediction point (i.e., $k_{out}$) 318. The prediction data window 314 corresponds to a number of motion samples to be used for a prediction. The prediction data window and thus window length, $k_w$, may correspond to a sliding window. The look ahead time period 316 corresponds to a number of sample periods between the prediction data window 314 (i.e., an end of the prediction data window 314) and the prediction 318. A relatively larger $k_w$ may produce a relatively better prediction results, however, the improvement may be somewhat asymptotic. In other words, increasing $k_w$ beyond a selected number may result in a lower improvement in prediction accuracy. In an embodiment, $k_w$, i.e., a second number of motion samples, may be in the range of 5 to 20. In one nonlimiting example, $k_w$ may be equal to 15.

The look-ahead length, h, may be measured from a last data point in the prediction data window $k_w$. In some situations, h may be related to imaging/therapeutic equipment latency. Imaging/therapeutic equipment latency may be specific to a particular imaging/therapeutic device. For example, latency may be in the range of 40 ms (milliseconds) to 500 ms, depending on the particular imaging/ therapeutic device. In an embodiment, h may be in the range of 1 to 20. For example, for a 30 ms sample interval, h equal to 2 corresponds to a look-ahead time of 60 ms. In another example, h equal to 10 corresponds to a look-ahead time of 300 ms.

Thus, a system may be configured to capture respiratory motion data and to predict, in real time, a future motion of a target region. The future motion information may then be used to facilitate imaging and/or provision of therapeutic energy to the target region. The motion of the target region may vary over the imaging/therapeutic session due, in part, to patient respiration. In an embodiment, the predicting may be performed by a recurrent neural network (RNN) circuitry that has been trained, in real time, using patient target region motion data. The training may be updated using a sliding window of motion data, to reflect relatively more current patient respiration and corresponding target region motion data.

Figures 4, 5:
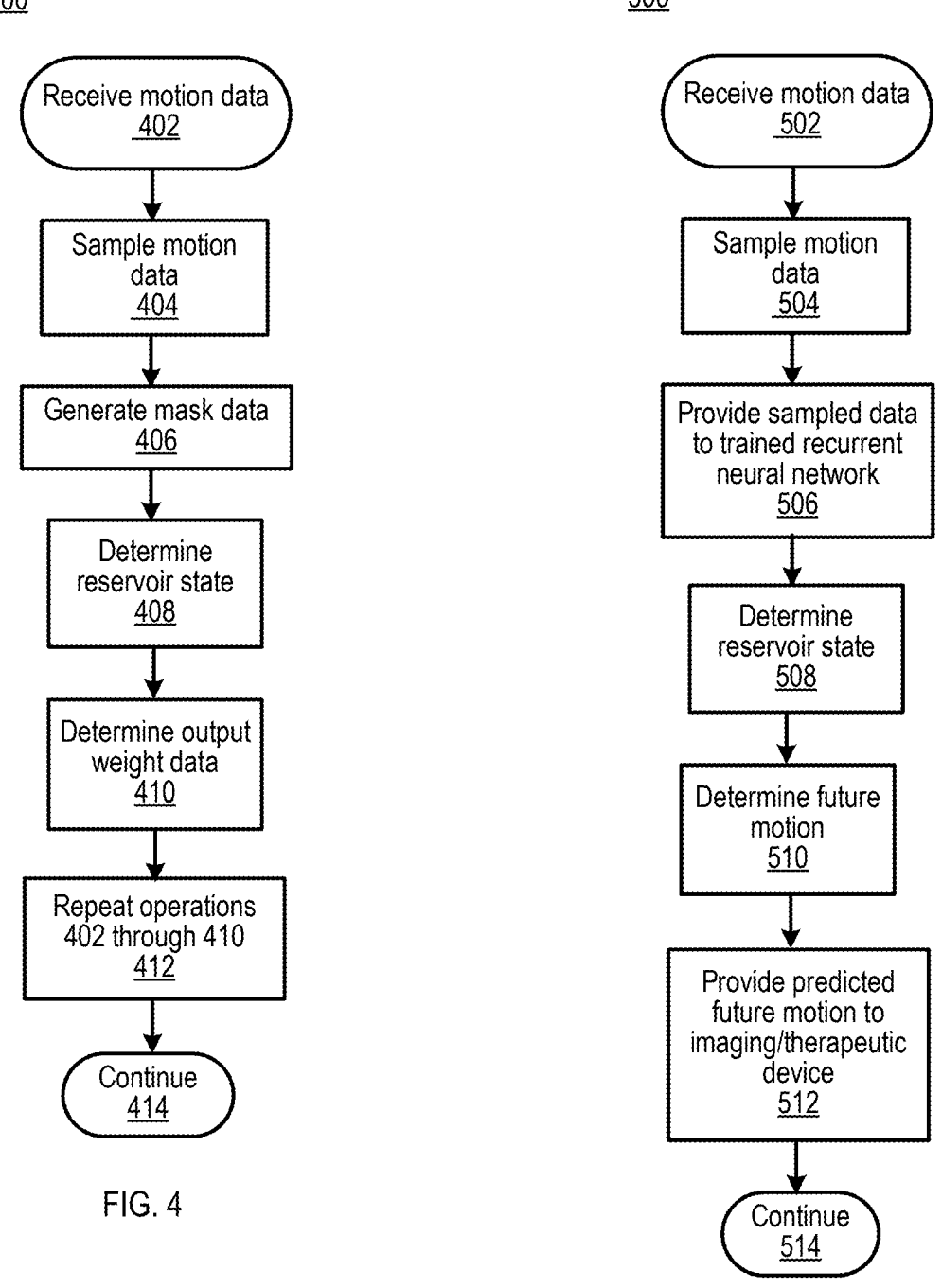
FIG. 4 is a flowchart of recurrent neural network training operations according to various embodiments of the present disclosure.
FIG. 5 is a flowchart of tumor movement prediction operations according to various embodiments of the present disclosure.

FIG. 4 is a flowchart 400 of recurrent neural network training operations according to various embodiments of the present disclosure. In particular, the flowchart 400 illustrates training a recurrent neural network based, at least in part, on a training data set. The operations may be performed, for example, by system controller circuitry 104 and recurrent neural network circuitry 102 of FIG. 1.

Operations of this embodiment may begin with receiving motion data at operation 402. Motion data may be sampled at operation 404. Mask data may be generated at operation 406. A reservoir state may be determined at operation 408. Output weight data may be determined at operation 410. Operation 412 may include repeating operations 402 through 410. Operations may then continue at operation 414. Thus, a recurrent neural network may be trained based, at least in part, on a training data set FIG. 5 is a flowchart 500 of tumor movement prediction operations according to various embodiments of the present disclosure. In particular, the flowchart 500 illustrates predicting a future target region motion by a recurrent neural network based, at least in part, on motion data. The operations may be performed, for example, by recurrent neural network 102 and system controller circuitry 104 of FIG. 1.

Operations of this embodiment may begin with receiving motion data at operation 502. Motion data may be sampled at operation 504. Sampled data may be provided to a trained recurrent neural network at operation 506. A reservoir state may be determined at operation 508. A future motion of a patient target region may be determined at operation 510. Operation 512 may include providing the predicted future motion to an imaging/therapeutic device. Operations may continue at operation 514. Thus, a trained recurrent neural network may be configured to predict a future motion of a patient target region based, at least in part, on a prediction data set.

As used in any embodiment herein, the term "module" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hard-wired circuitry, programmable circuitry such as a computer processor including one or more individual instruction processing cores, a microcontroller, a field programmable gate array (FPGA), state machine circuitry, and/or firmware that stores instructions executed by programmable circuitry. Circuitry may include electrical circuits and elements, optical fibers and elements and/or optical/electrical conversion circuitry. A module may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc.

Memory circuitry 124 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively system memory may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A method of imaging and/or provision of therapeutic energy to a target region based on real time predictions of respiratory motion, the method comprising:

measuring position data with position sensing circuitry, the measured position data corresponding to respiratory motion of a patient target area;

providing the measured position data from the position sensing circuitry to a system controller circuitry comprising a training module and a prediction module, the training module comprising instructions executable by one or more processors to manage training a recurrent neural network circuitry, and the prediction module comprising instructions executable by one or more processors to predict a future position of the patient target area based on the trained recurrent neural network circuitry;

providing sampled measured position data from the system controller circuitry to the recurrent neural network circuitry;

training, by the training module, the recurrent neural network circuitry in real time, the training based, at least in part, on a training data set, the training data set comprising a first number of motion samples, the motion samples being sampled from the measured position data;

predicting, by the prediction module, based on the trained recurrent neural network circuitry, a predicted future position of the patient target region at a future point in time based, at least in part, on a prediction data set, the future point in time a look ahead time period in the future relative to a prediction data window, the prediction data set comprising a second number of motion samples;

outputting the predicted future position of the patient target region to an imaging/therapeutic device, the therapeutic device using the predicted future position of the patient target region to control imaging and/or provision of therapeutic energy to the target region by the imaging/therapeutic device.

2. The method of claim 1, further comprising updating, by the training module, the training of the recurrent neural network circuitry, at an update time interval, the updating based, at least in part, on a current internal state of the recurrent neural network circuitry.

3. The method of claim 2, wherein the updating comprises determining a plurality of output weight values using a sliding training data window corresponding to the first number of motion samples.

4. The method of claim 1, wherein the prediction data window corresponds to a sliding window.

5. The method of claim 1, wherein a length of the look ahead time period is related to a latency of imaging and/or therapeutic.

6. The method of claim 2, wherein the update time interval is related to a motion data sample interval.

7. The method of claim 1, wherein the recurrent neural network corresponds to a reservoir computing network.

8. The method of claim 3, wherein a time duration of the training data window is less than or equal to 30 seconds.

9. The method of claim 1, wherein the second number of motion samples is in the range of 5 to 20.

10. The method of claim 6, wherein the motion data sample rate is in the range of 10 to 40 samples per second.

11. A system of imaging and/or provision of therapeutic energy to a target region based on real time predictions of respiratory motion, the system comprising:

position sensing circuitry, configured to measure position data corresponding to respiratory motion of a patient target area;

a system controller circuitry configured to receive measured position data from the position sensing circuitry and to provide a predicted future position of the patient target region to an imaging/therapeutic device, thereby facilitating the imaging and/or provision of therapeutic energy to the target region by the imaging/therapeutic device, the system controller circuitry including:

a training module; and a recurrent neural network circuitry, wherein the training module comprises instructions executable by one or more processors to train the recurrent neural network circuitry in real time, the training based, at least in part, on a training data set, the training data set comprising a first number of motion samples, the motion samples being sampled from the measured position data; and wherein the trained recurrent neural network circuitry is configured to predict a future motion of the patient target region at a future point in time based, at least in part, on a prediction data set, the future point in time being a look ahead time period in the future relative to a prediction data window, and the prediction data set comprising a second number of motion samples.

12. The system of claim 11, wherein the training module comprises instructions executable by one or more processors to update the training of the recurrent neural network circuitry, at an update time interval, the updating based, at least in part, on a current internal state of the recurrent neural network circuitry.

13. The system of claim 12, wherein the updating comprises determining a plurality of output weight values using a sliding training data window corresponding to the first number of motion samples.

14. The system of claim 11, wherein the prediction data window corresponds to a sliding window.

15. The system of claim 11, wherein a length of the look ahead time period is related to a latency of imaging and/or therapeutic equipment.

16. The system of claim 12, wherein the update time interval is related to a motion data sample interval.

17. The system of claim 11, wherein the recurrent neural network corresponds to a reservoir computing network.

18. The system of claim 13, wherein a time duration of the training data window is less than or equal to 30 seconds.

19. The system of claim 11, wherein the second number of motion samples is in the range of 5 to 20.

20. The system of claim 16, wherein the motion data sample rate is in the range of 10 to 40 samples per second.

* * * * *